(12) United States Patent
Axelrod et al.

(10) Patent No.: US 8,372,389 B2
(45) Date of Patent: Feb. 12, 2013

(54) METHODS FOR THE TREATMENT OF RADIATION OR CHEMOTHERAPY-INDUCED TISSUE DAMAGE

(75) Inventors: Jonathan H. Axelrod, Jerusalem (IL); Eithan Galun, Har-Adar (IL); Stefan Rose-John, Schellhorn (DE); Ytzhack Marmary, Motza Ilit (IL)

(73) Assignees: Hadasit Medical Research Services and Development Ltd., Jerusalem (IL); Christian-Albrechts-Universitat Zu Kiel, Kiel (DE)

( * ) Notice: Subject to any disclaimer, the term of this patent is extended or adjusted under 35 U.S.C. 154(b) by 0 days.

(21) Appl. No.: 12/745,049

(22) PCT Filed: Nov. 27, 2008

(86) PCT No.: PCT/IL2008/001556
§ 371 (c)(1), (2), (4) Date: Apr. 4, 2011

(87) PCT Pub. No.: WO2009/069133
PCT Pub. Date: Jun. 4, 2009

(65) Prior Publication Data
US 2011/0184220 A1    Jul. 28, 2011

Related U.S. Application Data

(60) Provisional application No. 60/990,631, filed on Nov. 28, 2007.

(51) Int. Cl.
*A61K 38/20* (2006.01)

(52) U.S. Cl. .......................................... 424/85.2; 514/1.1

(58) Field of Classification Search .................. None
See application file for complete search history.

(56) References Cited

U.S. PATENT DOCUMENTS

| 5,171,840 | A | 12/1992 | Kishimoto |
| 5,919,763 | A * | 7/1999 | Galun et al. .................. 424/85.2 |
| 5,994,409 | A | 11/1999 | Stogniew |
| 6,054,294 | A | 4/2000 | Chang |
| 7,112,436 | B1 | 9/2006 | Rose-John |
| 2004/0157326 | A1 | 8/2004 | Miura |

FOREIGN PATENT DOCUMENTS

| EP | 1598364 | 11/2005 |
| WO | 99/62534 | 12/1999 |
| WO | 03/029281 | 4/2003 |
| WO | 03/092579 | 11/2003 |
| WO | 2005/105135 | 11/2005 |
| WO | 2005/113591 | 12/2005 |
| WO | 2006/134601 | 12/2006 |

OTHER PUBLICATIONS

Berns, Kenneth I. and Giraud, Catherine, "Adenovirus and adeno-associated virus as vectors for gene therapy", Ann. N.Y. Acad. Sci. 772:95-104 (1995).
Brouazin-Jousseaume, V. et al., "GSH level and IL-6 production increased in Sertoli cells and astrocytes after gamma irradiation", Anticancer Res. 22: 257-262 (2002).
Database WPI, week 200708 Thomson Scientific, London, GB; AN 2007-083150 XP002661758.
Fischer, Martina et al., "A bioactive designer cytokine for human hematopoietic progenitor cell expansion. Nat. Biotechnol", 15(2):142-147 (1997).
Jones SA and Rose-John S., "The role of soluble receptors in cytokine biology: the agonistic properties of the sIL-6R/IL-6 complex. Biochim Biophys Acta", 1592(3):251-263 (2002).
Legue, F. et al., "IL-6 a key cytokine in in vitro and in vivo response of Sertoli cells to external gamma irradiation", Cytokine 16(6):232-238 (2001).
Nagler Rafael M. "Effects of radiotherapy and chemotherapeutic cytokines on a human salivary cell line", Anticancer Res. 18(1A):309-14 (1998).
Neta, Ruth et al., "Role of interleukin 6 (IL-6) in protection from lethal irradiation and in endocrine responses to IL-1 and tumor necrosis factor", J. Exp. Med. 175(3):689-694 (1992).
Peters, Malte et al., "In Vivo and In Vitro Activities of the gp130-Stimulating Designer Cytokine Hyper-IL-6", J. Immunol. 161(7):3575-3581 (1998).
International Search Report, Appln. No. PCT/IL2008/001556 dated Jun. 24, 2009 (1 page).
European Search report, Appln. No. EP 08853559.6 dated Oct. 21, 2011 (3 pages).

* cited by examiner

*Primary Examiner* — Prema Mertz
(74) *Attorney, Agent, or Firm* — Rodney J. Fuller; Booth Udall Fuller PLC

(57) ABSTRACT

The present invention relates to methods for preventing or treating toxicities associated with exposure to ionizing radiation or to chemotherapy. Particularly, the present invention relates to methods for preventing or treating toxicities associated with radiation or chemotherapy comprising administering to a subject in need of such treatment polypeptide complexes comprising an IL-6 linked to a soluble IL-6 receptor, the polypeptide complexes capable of preventing or treating toxicities, particularly xerostomia.

5 Claims, 5 Drawing Sheets

```
  1 GTCGACGC ATG GAG TGG TAG CCGAGGAGGAAGC ATG CTG GCC GTC GGC TGC GCG CTG CTG GCT GCC CTG CTG GCC GCG         78
  1                                        M   L   A   V   G   C   A   L   L   A   A   L   L   A   A          15

79 CCG GGA GCG GCG CTG GCC CCA AGG CGC CCT GCG CAG GAG GTG GCA AGA GGC GTG CTG ACC AGT CTG CCA GGA           153
 16  P   G   A   A   L   A   P   R   R   P   A   Q   E   V   A   R   G   V   L   T   S   L   P   G           40

154 GAC AGC GTG ACT CTG ACC TGC ACC CCG GGG GTA GAG GAC CCG GAA GAC AAT GCC ACT GTT CAC TGG GTG CTC AGG AAG CCG 228
 41  D   S   V   T   L   T   C   T   P   G   V   E   D   P   E   D   N   A   T   V   H   W   V   L   R   K   P 65

229 GCT GCA GGC TCC CAC CCC AGC TGC GGC AGA TGG GCT GGC ATG GGA GGC ATG AGG AGG CTG CTG AGG TCG CAG CTC CAC GAC 303
 66  A   A   G   S   H   P   S   C   G   R   W   A   G   M   G   G   M   R   R   L   L   R   S   Q   L   H   D 90

304 TCT GGA AAC TAT TCA TGC CGG TAC TGC TCC CCA CCA GCT GGG ACT GTG CTG GAT GTT CCC CCC GAG                    378
 91  S   G   N   Y   S   C   R   Y   C   S   P   P   A   G   T   V   L   D   V   P   P   E                     115

379 GAG CCC CAG CTC TCC TGC TTC TGG CGG AAG AGC CCC CTC GTG GTT TGT GAG TGG GGT CCT CGG AGC ACC CCA              453
116  E   P   Q   L   S   C   F   W   R   K   S   P   L   V   V   C   E   W   G   P   R   S   T   P              140

454 TCC CTG ACA AAG GCT GTG CTC TTG AAG TTT CAG AAC AGT CCG GCC GAA GAC TTC CAG GAG CCG TGC                    528
141  S   L   T   K   A   V   L   L   K   F   Q   N   S   P   A   E   D   F   Q   E   P   C                     165

529 CAG TAT TCC CAG GAG TCC CAG AAG TTC TCC TGC CAG TTA GCA GTC ACC AGC TCT GGT TGT GGA ATC TTG CAG             603
166  Q   Y   S   Q   E   S   Q   K   F   S   C   Q   L   A   V   T   S   S   G   C   G   I   L   Q              190

604 TCC ATG TGC GTC GCC AGT ATC AAC ACA GTC ACT TTC AGC AAG AAA ACT CAA ACC TTT CAG TGG TGT AGT GTC ACC CGG CAA GAC TTC 678
191  S   M   C   V   A   S   I   N   T   V   T   F   S   K   K   T   Q   T   F   Q   W   C   S   V   T   R   Q   D   F 215

679 CCT GAT CCG CCT GCC AAC ATC ACT ACT GCC GTG ACT CCC AGA AAC CCC CGC TGG CTC AGT GTC ACC TGG CAA GAC          753
216  P   D   P   P   A   N   I   T   T   A   V   T   P   R   N   P   R   W   L   S   V   T   W   Q   D          240

754 CCC CAC TCC TGG AAC TCA TCT TTC TAC AGA CTA CGG TTT GAG CTC CGC TAT CGG GCT GAA CGG TCA AAG ACA TTC          828
241  P   H   S   W   N   S   S   F   Y   R   L   R   F   E   L   R   Y   R   A   E   R   S   K   T   F          265

829 ACA ACA TGG ATG GTC AAG GAC CTC CAG CAT CAC TGT GTC ATC CAC GAC GCC TGG AGC GGC CTG AGG CAC GTG              903
266  T   T   W   M   V   K   D   L   Q   H   H   C   V   I   H   D   A   W   S   G   L   R   H   V               290

904 CAG CTT CGT GCC ATG CGT GCC CAG GAG GAG TTC GGG CAA GGC GAG TGG AGC GAG GAG TGG AGC CCG GAG ATG GGC ACG CCT TGG 978
291  Q   L   R   A   M   R   A   Q   E   E   F   G   Q   G   E   W   S   E   E   W   S   P   E   M   G   T   P   W 315

979 ACA GAA TCC AGG AGT CCT CCA GCT CGA GGA GGT TCT GGA GGT TCT GTC GAG CCA GTA CCC CCA                        1053
316  T   E   S   R   S   P   P   A   R   G   G   S   G   G   S   V   E   P   V   P   P                         340
```

METHODS FOR THE TREATMENT OF RADIATION OR CHEMOTHERAPY-INDUCED TISSUE DAMAGE

RELATED APPLICATION DATA

This application is the U.S. National Stage of PCT/IL2008/001556 filed Nov. 27, 2008, which claims the benefit of U.S. Provisional Application No. 60/990,631, filed Nov. 28, 2007, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 17,434 byte ASCII (text) file named "Seq_List" created on May 27, 2010.

FIELD OF THE INVENTION

The present invention relates to methods for preventing or treating toxicities associated with exposure to ionizing radiation or to chemotherapy. Particularly, the present invention relates to methods for preventing or treating toxicities associated with radiation or chemotherapy comprising administering to a subject in need of such treatment polypeptide complexes comprising an IL-6 linked to a soluble IL-6 receptor, the polypeptide complexes capable of preventing or treating toxicities, particularly xerostomia.

BACKGROUND OF THE INVENTION

Modern cancer therapy relies strongly on the use of ionizing irradiation, either alone or in combination with surgery or chemotherapy, as a primary strategy for the treatment of malignancies of various types. Ionizing radiation induces multiple and varying biochemical events in various cell types determining the ability of the cell to survive the radiation challenge. As a result, different normal and malignant tissues in the body display variable radio-sensitivity. For example, radiotherapy to the gastro-intestinal (GI) tract can cause a potentially fatal GI syndrome, nephrotoxicity, esophagitis and lung complications. After irradiation, cells can be lost due to apoptosis, or through interference with cellular repair mechanisms or subsequent cell division leading to eventual cell death. A recent study on gastrointestinal tract irradiation damage in mice proposed that endothelial cell apoptosis is the primary lesion of irradiation induced damage followed by epithelial damage. Side effects of radiotherapy relate to the damage caused to normal surrounding tissues while irradiating the target tumor.

Each year, newly diagnosed cases of oral and laryngeal cancer are reported for more than 41,000 Americans and between 350,000-400,000 world wide. Irradiation-induced xerostomia, or dry mouth, is a direct consequence of the high sensitivity of the salivary glands to ionizing radiation, and is the most common toxicity associated with standard fractionated radiation therapy to patients suffering from cancers of the head and neck.

Radiation produces changes in the salivary gland secretory cells, resulting in a reduction in salivary output and increased viscosity of the saliva. Xerostomia varies from scant to complete and is potentially debilitating. Acute radiation-induced xerostomia is associated with an inflammatory response, while late xerostomia, which can occur up to one year after radiation therapy, results in fibrosis of the salivary glands and is usually permanent. Both the parotid and submandibular glands show similar morphologic alterations after irradiation, but the exact mechanism mediating radiation induced cell death is not yet known. A correlation between the radiation induced salivary gland damage and the role of intracellular redox-active metal ions has been reported. One hypothesis explaining the mechanism for the salivary gland radio-sensitivity suggests that radiation causes the disruption of salivary gland granules, the contents of which leak into the cytoplasm causing redistribution in the cell of loosely bound metal ions, including iron and copper that reach the DNA and promote damage by generation of free radicals and reactive oxygen species (ROS). Other factors such as the enhanced production of p53 and calcium overload are also thought to be involved. Unlike the changes in the GI tract, chronic acinar atrophy seen in the parotid is considered to be a consequence of direct, irreversible, and early injury, not the result of radiation-induced changes in the vasculature.

The most important factors that determine the severity of salivary gland damage from therapeutic irradiation in patients are the dose of radiation delivered and the volume of gland exposed to the radiation. When the total radiation dose exceeds 52 Gy, salivary flow is reduced or even totally inhibited so that no saliva is secreted from the salivary glands to the mouth. These changes are usually permanent. As a result, patients suffer from acute effects and face residual impairments. Late effects include nutritional problems due to difficulty in chewing, swallowing and tasting, and communication problems due to severe difficulties of speech. Severe ulcers and infections develop in the oral mucosa due to the impairment of the oral immune system, aggravating the patient's state of health. In a recent survey on quality of patient life issues, 10-24% of irradiated head and neck cancer patients placed high importance on the oral side effects of their treatment.

U.S. Pat. No. 5,994,409 to Stogniew et al. discloses methods for treating toxicities associated with the exposure of a human to antineoplastic radiation therapy which comprises administering to said human of an aminothiol compound, preferably amifostine. U.S. Pat. No. 5,994,409 further discloses methods for treating xerostomia induced in a human by antineoplastic chemotherapy or antineoplastic radiation therapy comprising administering to said human an aminothiol compound, preferably amifostine.

While amifostine has been shown to be useful as a radiation protectant in cancer patients receiving radiation therapy, it has also been reported that intravenous administration of amifostine suffers from undesirable side effects such as nausea, vomiting, emesis, hypotension, flushing, chills, dizziness and sneezing. In order to reduce the side effects associated with intravenous administration of amifostine, U.S. Pat. No. 6,573,253 to Stogniew et al. discloses methods for protecting against or treating the toxicities associated with ionizing radiation in a subject comprising subcutaneously administering to the subject an aminothiol compound. Among the toxicities disclosed is xerostomia.

International Patent Application Publication No. WO 2005/113591 of Mackiewicz et al. discloses uses of H11, a complex polypeptide consisting of soluble interleukin-11 receptor (sIL-11R) and IL-11, in treating or preventing a proliferative disease, a cytopathy, and radiation damage, though no specific enablement or guidance is provided for treating or preventing radiation damage.

The cytokine interleukin-6 (IL-6) was shown to exert radio-protective activity only when administered with IL-1 and TNF to mice exposed to total-body irradiation (Neta et al., J. Exp. Med. 175: 689-694, 1992; Legue et al., Cytokine 16: 232-238, 2001). However, when IL-6 was administered by itself to mice exposed to total-body irradiation, it was ineffective as a radio-protectant (Neta et al., ibid.). It has been hypothesized that IL-6 contributes to the adaptive response to oxidative stress generated by gamma-irradiation (Brouazin et al., Anticancer Res. 22: 257-262, 2002).

IL-6 is a member of a family of cytokines that act via receptor complexes containing at least one subunit of the transmembrane signal transducing protein, gp130, which is found in almost all organs, including heart, kidney, spleen, liver, lung and brain. On target cells, IL-6 acts by binding to a specific transmembrane cognate receptor (gp80 or IL-6Rα), hereafter IL-6R, which triggers the homodimerization of gp130 (also called IL-6Rβ) and leads to the activation of the Jak/Stat signaling pathway, particularly of STAT-3. Unlike gp130, the endogenous expression of gp80 is naturally found in relatively few tissues in the body, including liver, intestine, and some B cells and T cells. Thus, because of the lack of the gp80 expression, only a few cell populations in the body would be expected to respond to IL-6 stimulation. However, in addition to its membrane bound form, the IL-6R is also found in a soluble form (sIL-6R), which when complexed with IL-6, is capable of stimulating cells via interaction with gp130. Importantly then, in a process called IL-6 trans-signaling, IL-6/sIL-6R complexes are capable of acting as an agonist on cell types that, although they express gp130, would not inherently respond to IL-6 alone.

A recombinant fusion protein called Hyper-IL-6 consisting of the human IL-6 linked by a flexible peptide chain to sIL-6R was shown to be a super agonistic designer cytokine (Fischer, M., et al. Nat. Biotechnol. 15: 142-145, 1997). Hyper-IL-6 is fully active on gp130-expressing cells at concentrations 100 to 1000 fold lower than the combination of unlinked IL-6 and sIL-6R, and exhibits a super agonistic effect both in vitro and in vivo, due to the 100 times higher affinity of the IL-6/sIL-6R complex to gp130 and due to its prolonged half-life in vivo (Peters, M., et al. J. Immunol. 161: 3575-3581, 1998).

U.S. Pat. No. 5,919,763 to Galun et al. discloses methods for treating an injury to a liver of a subject comprising administering to the subject a pharmaceutical composition comprising an IL-6/sIL-6R complex, preferably Hyper-IL-6.

International Application Publication No. WO 99/62534 to Galun et al. discloses methods for treating an injury to a liver of a subject comprising administering to the subject a pharmaceutical composition comprising an IL-6/sIL-6R complex, preferably Hyper-IL-6. WO 99/62534 further discloses methods of gene therapy for treating an injury to a liver of a subject comprising administering to the subject a vector carrying Hyper-IL-6 chimera gene.

International Application Publication No. WO 03/029281 to Axelrod et al. discloses a therapeutic composition comprising an IL-6 family member, preferably an IL-6/sIL-6 complex, and a liver regenerating factor. WO 03/029281 further discloses methods for treating a pathological condition in a subject comprising administering to the subject a therapeutic composition comprising an IL-6 family combination component and a liver regenerating factor, wherein at least one of the IL-6 family combination component and the liver regenerating factor is administered encoded by a plasmid.

International Application Publication No. WO 2006/134601 to Axelrod et al. discloses methods for preventing or treating renal failure comprising administering to a subject a pharmaceutical composition comprising a complex which comprises a member of the IL-6 family linked to a soluble receptor of the member of the IL-6 family. Preferably, the member of IL-6 family linked to a soluble receptor of the member of the IL-6 family is an IL-6/sIL-6 complex.

Nowhere in the background art is it disclosed or suggested that IL-6/sIL-6 receptor complexes are useful for protecting against or treating toxicities associated with ionizing radiation and chemotherapy.

SUMMARY OF THE INVENTION

The present invention provides methods for diminishing, preventing or treating toxicities associated with exposure to ionizing radiation or to chemotherapy comprising administering to a subject in need thereof a polypeptide complex comprising an IL-6 linked to a soluble IL-6 receptor. The present invention further provides methods for diminishing, preventing or treating toxicities associated with exposure to ionizing radiation or to chemotherapy comprising administering to a subject in need thereof an isolated polynucleotide encoding a polypeptide complex comprising IL-6 and soluble IL-6 receptor complex.

It is now disclosed for the first time that administering to a subject a polypeptide complex comprising human IL-6 polypeptide as set forth in SEQ ID NO:1 linked to human soluble IL-6 receptor as set forth in SEQ ID NO:2 prior to exposure of the subject to ionizing radiation protects the subject from damage to the salivary glands, hence prevents the development of the dry mouth disorder, also known as xerostomia. The polypeptide complex comprising human IL-6 linked to human soluble IL-6 receptor is useful not only for protecting subjects against xerostomia, but also against other toxicities associated with ionizing radiation. Similarly, the polypeptide complex of the present invention is also useful in protecting subjects against toxicities associated with chemotherapy. While the present invention is exemplified herein below by the radio-protective effect of the polypeptide complex designated Hyper-IL-6 as set forth in SEQ ID NO:3 against acute xerostomia, other toxicities such as mucositis, neurotoxicity, ototoxicity, pulmonary toxicity, alopecia, cytopenia, and cardiotoxicity are encompassed in the present invention.

The present invention is based in part on the findings that while in untreated rats and mice subjected to X-irradiation, salivary gland function was reduced significantly, rats and mice pretreated with intra-ductal infusion of Hyper-IL-6 to submandibular glands displayed only minor reduction in salivary gland function. The present invention thus demonstrates that treatment of the salivary glands with Hyper-IL-6 prior to irradiation renders nearly complete protection of these glands from irradiation-induced damage and maintains gland function.

According to one aspect, the present invention provides a method for preventing or treating a toxicity associated with ionizing radiation in a subject comprising administering to a subject in need of such treatment a therapeutically effective amount of a pharmaceutical composition comprising as an active agent a polypeptide complex comprising human IL-6 as set forth in SEQ ID NO:1 or a biologically active analog or fragment thereof, and human soluble IL-6 receptor (sIL-6R) as set forth in SEQ ID NO:2 or a biologically active analog or fragment thereof, and a pharmaceutically acceptable carrier, wherein the toxicity is selected from the group consisting of xerostomia, mucositis, neurotoxicity, ototoxicity, myelosuppression, cardiotoxicity, pulmonary toxicity, cytopenia, alopecia, vasculopathy, infertility, and toxicities to the esophagus, intestine, and pancreas.

According to one embodiment, the fragment of human IL-6 comprises amino acid residues 29-212 of human IL-6 as set forth in SEQ ID NO:4. According to additional embodiments, the fragment of human sIL-6R comprises amino acid residues 113-323 of human sIL-6R as set forth in SEQ ID NO:5 or amino acid residues 114-323 of human sIL-6R as set forth in SEQ ID NO:6. According to another embodiment, the polypeptide complex further comprises a 13-mer peptide linker of the amino acid sequence as set forth in SEQ ID NO:7. According to a currently exemplary embodiment, the polypeptide complex useful for preventing or treating the toxicity associated with ionizing radiation is Hyper-IL-6 as set forth in SEQ ID NO:3 consisting of amino acid residues 1-323 of human sIL-6R, a 13-mer peptide linker, and amino acid residues 29-212 of human IL-6.

According to some embodiment, the toxicity associated with ionizing radiation is xerostomia selected from the group consisting of acute xerostomia and late xerostomia. According to a currently exemplary embodiment, the toxicity is acute xerostomia.

According to additional embodiments, the route of administering the pharmaceutical composition to the subject is selected from the group consisting of direct administration into or in the vicinity of a tissue having said toxicity, topical, intradermal, intramuscular, intraperitoneal, intravenous, subcutaneous, intranasal, epidural, transdermal and oral administration.

According to further embodiments, the pharmaceutical composition is formulated in a form selected from the group consisting of solutions, suspensions, emulsions, tablets, capsules, powders, suppositories, and sustained-release formulations.

According to yet further embodiments, the pharmaceutical composition is administered to the subject prior to exposure of said subject to ionizing radiation. Alternatively, the pharmaceutical composition is administered simultaneously with exposure of the subject to ionizing radiation. Further alternatively, the pharmaceutical composition is administered after exposure of the subject to ionizing radiation. It is to be understood that the pharmaceutical composition can be administered prior to and simultaneously with exposure of the subject to ionizing radiation, or simultaneously and after exposure of the subject to ionizing radiation, or as required so as to protect against or treat said toxicity.

According to another aspect, the present invention provides a method for preventing or treating a toxicity associated with administration of a chemotherapeutic agent to a subject, the method comprises administering to a subject in need of such treatment a therapeutically effective amount of a pharmaceutical composition comprising as an active agent a polypeptide complex comprising human IL-6 as set forth in SEQ ID NO:1 or a biologically active analog or fragment thereof, and human sIL-6R as set forth in SEQ ID NO:2 or a biologically active analog or fragment thereof, and a pharmaceutically acceptable carrier, wherein the toxicity is selected from the group consisting of xerostomia, mucositis, neurotoxicity, ototoxicity, myelosuppression, cardiotoxicity, pulmonary toxicity, cytopenia, alopecia, vasculopathy, infertility, and toxicities to the esophagus, intestine, and pancreas. According to a currently exemplary embodiment, the polypeptide complex useful for preventing or treating the toxicity associated with administration of a chemotherapeutic agent is Hyper-IL-6 as set forth in SEQ ID NO:3.

According to some embodiment, the toxicity associated with administration of a chemotherapeutic agent is xerostomia selected from the group consisting of acute xerostomia and late xerostomia.

According to additional embodiments, the pharmaceutical composition is administered to the subject prior to administration of the chemotherapeutic agent. Alternatively, the pharmaceutical composition is administered simultaneously with administration of the chemotherapeutic agent. Further alternatively, the pharmaceutical composition is administered after administration of the chemotherapeutic agent. It is to be understood that the pharmaceutical composition can be administered prior to and simultaneously with administration of the chemotherapeutic agent, or simultaneously and after administration of the chemotherapeutic agent, or as required so as to protect against or treat said toxicity.

According to some embodiments, the chemotherapeutic agent is selected from the group consisting of taxanes, alkylating agents, alkyl sulfonates, nitrosoureas, antimetabolites, pyrimidine analogs, purine analogs, natural products, antibiotics, and platinum coordination complexes. According to exemplary embodiments, the chemotherapeutic agent is selected from the group consisting of cisplatin, carboplatin, paclitaxel, vinblastine, vincristine, and methotrexate.

According to another aspect, the present invention provides use of a polypeptide complex comprising human IL-6 as set forth in SEQ ID NO:1 or a biologically active analog or fragment thereof, and human soluble IL-6 receptor (sIL-6R) as set forth in SEQ ID NO:2 or a biologically active analog or fragment thereof, for the preparation of a medicament for preventing or treating a toxicity associated with ionizing radiation, the toxicity selected from the group consisting of xerostomia, mucositis, neurotoxicity, ototoxicity, myelosuppression, cardiotoxicity, pulmonary toxicity, cytopenia, alopecia, vasculopathy, infertility, and toxicities to the esophagus, intestine, and pancreas. According to a certain embodiment, the polypeptide complex is Hyper-IL-6 as set forth in SEQ ID NO:3 useful for the prevention or treatment of the toxicity associated with ionizing radiation. According to an exemplary embodiment, the toxicity associated with ionizing radiation is xerostomia.

According to yet another aspect, the present invention provides use of a polypeptide complex comprising human IL-6 as set forth in SEQ ID NO:1 or a biologically active analog or fragment thereof, and soluble IL-6 receptor (sIL-6R) as set forth in SEQ ID NO:2 or a biologically active analog or fragment thereof, for the preparation of a medicament for preventing or treating a toxicity associated with administration of a chemotherapeutic agent, the toxicity selected from the group consisting of xerostomia, mucositis, neurotoxicity, ototoxicity, myelosuppression, cardiotoxicity, pulmonary toxicity, cytopenia, alopecia, vasculopathy, infertility, and toxicities to the esophagus, intestine, and pancreas. In one embodiment, Hyper-IL-6 as set forth in SEQ ID NO:3 is useful for the prevention and treatment of the toxicity associated with administration of a chemotherapeutic agent. According to a certain embodiment, the toxicity associated with administration of a chemotherapeutic agent is xerostomia.

According to still a further aspect, the present invention provides a method for preventing or treating a toxicity associated with ionizing radiation or with administration of a chemotherapeutic agent comprising administering to a subject in need of such treatment a therapeutically effective amount of a pharmaceutical composition comprising as an active agent an isolated polynucleotide encoding a polypeptide complex comprising human IL-6 as set forth in SEQ ID NO:1 or a biologically active analog or fragment thereof, and human soluble IL-6 receptor (sIL-6R) as set forth in SEQ ID NO:2 or a biologically active analog or fragment thereof; and a pharmaceutically acceptable carrier, wherein the toxicity is selected from the group consisting of xerostomia, mucositis, neurotoxicity, ototoxicity, myelosuppression, cardiotoxicity, pulmonary toxicity, cytopenia, alopecia, vasculopathy, infertility, and toxicities to the esophagus, intestine, and pancreas. According to one embodiment, the toxicity associated with ionizing radiation is xerostomia. According to a certain embodiment, the isolated polynucleotide has the nucleotide sequence as set forth in SEQ ID NO:8.

According to yet a further aspect, the present invention provides a method for preventing or treating a toxicity associated with ionizing radiation or with administration of a chemotherapeutic agent comprising administering to a subject in need of such treatment a therapeutically effective amount of a pharmaceutical composition comprising as an active agent an expression vector comprising an isolated polynucleotide encoding a polypeptide complex comprising human IL-6 as set forth in SEQ ID NO:1 or a biologically active analog or fragment thereof, and human soluble IL-6 receptor (sIL-6R) as set forth in SEQ ID NO:2 or a biologically active analog or fragment thereof; and a pharmaceutically acceptable carrier, wherein the toxicity is selected from the group consisting of xerostomia, mucositis, neurotoxicity, ototoxicity, myelosuppression, cardiotoxicity, pulmonary toxicity, cytopenia, alopecia, vasculopathy, infertility, and toxicities to the esophagus, intestine, and pancreas. According to one embodiment, the toxicity associated with ionizing radiation is xerostomia. According to a certain embodiment, the isolated polynucleotide is set forth in SEQ ID NO:8.

According to another aspect, the present invention provides use of an isolated polynucleotide encoding a polypeptide complex comprising human IL-6 as set forth in SEQ ID NO:1 or a biologically active analog or fragment thereof, and human soluble IL-6 receptor (sIL-6R) as set forth in SEQ ID NO:2 or a biologically active analog or fragment thereof, for the preparation of a medicament for preventing or treating a toxicity associated with ionizing radiation or with chemotherapy. According to a certain embodiment, the isolated polynucleotide useful for treating xerostomia has the nucleotide sequence as set forth in SEQ ID NO:8.

According to a further aspect, the present invention provide use of an expression vector comprising an isolated polynucleotide encoding a polypeptide complex comprising human IL-6 as set forth in SEQ ID NO:1 or a biologically active analog or fragment thereof, and human soluble IL-6 receptor (sIL-6R) as set forth in SEQ ID NO:2 or a biologically active analog or fragment thereof, for the preparation of a medicament for preventing or treating a toxicity associated with ionizing radiation or with chemotherapy. According to a certain embodiment, the isolated polynucleotide within the expression vector has the nucleotide sequence as set forth in SEQ ID NO:8.

These and other embodiments of the present invention will be better understood in relation to the figures, description, examples and claims that follow.

BRIEF DESCRIPTION OF THE FIGURES

Figure 4:
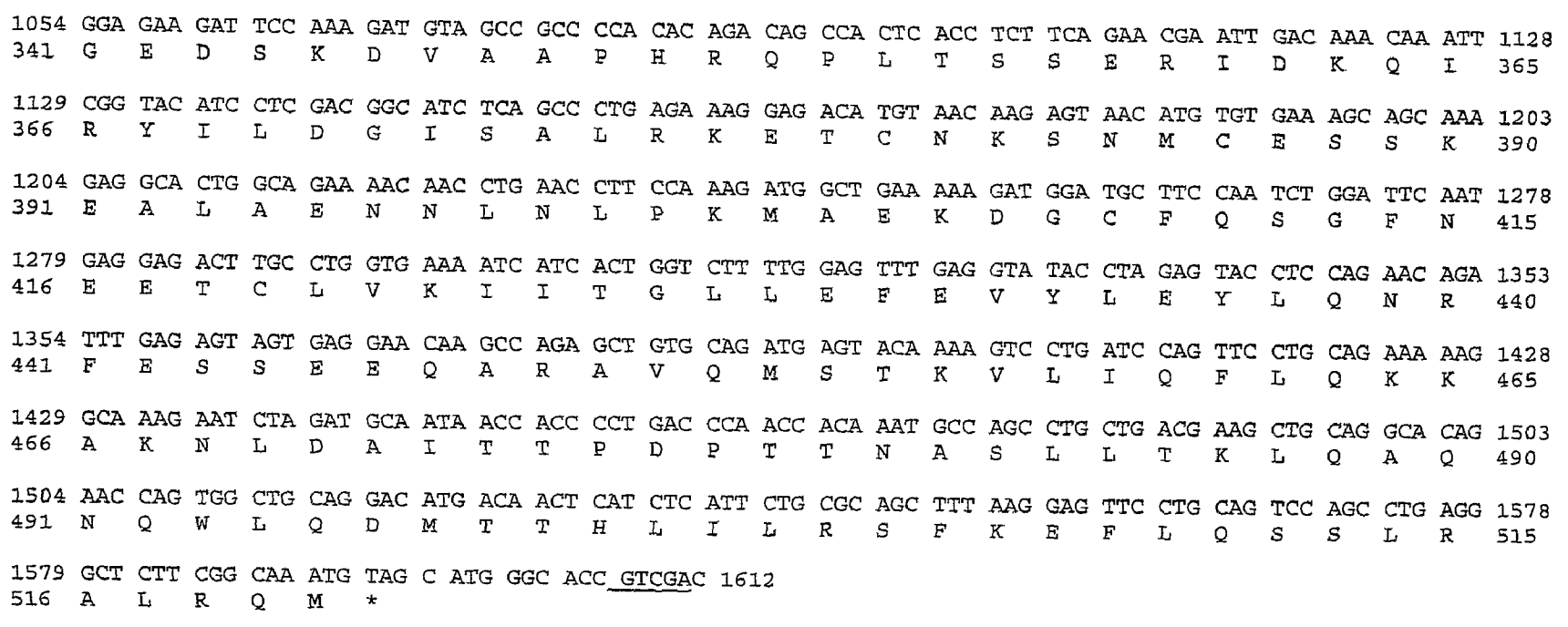

FIG. 4 shows the amino acid and nucleotide sequence of Hyper-IL-6. Recognition sites for the restriction endonuclease Sal I (GTCGAC), signal peptide and the synthetic linker used to connect the soluble human IL-6R at its COOH-terminus with the NH2-terminus of human IL-6 are underlined.

DETAILED DESCRIPTION OF THE INVENTION

Figure 1:
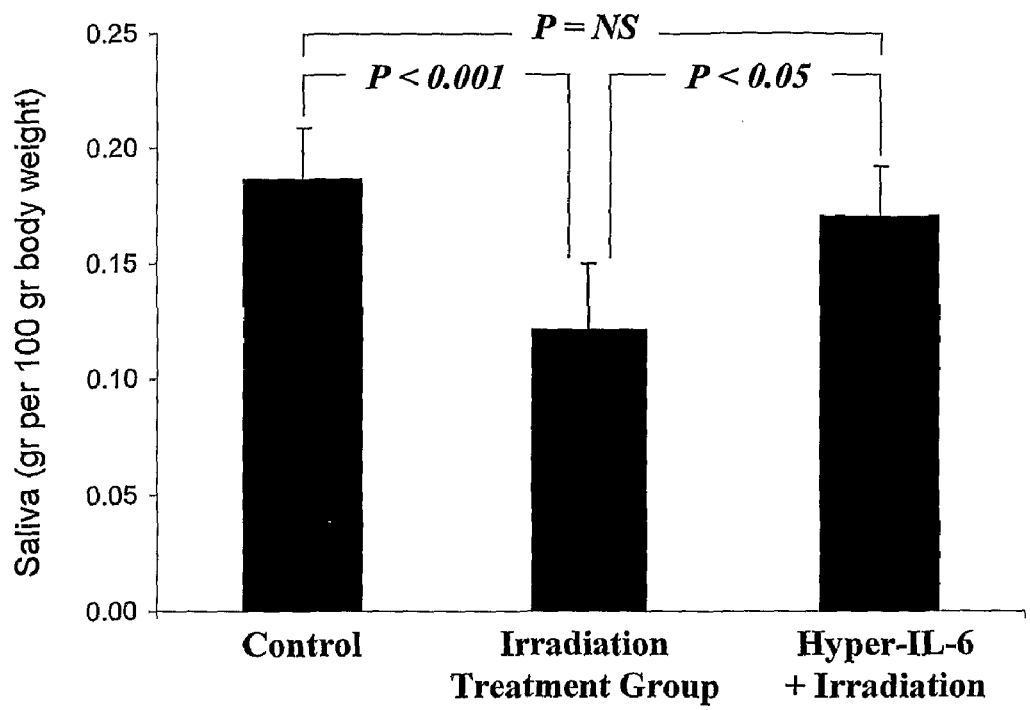
FIG. 1 shows the effect of Hyper-IL-6 on irradiation-induced xerostomia in rats. Male rats were infused in the submandibular gland with either Hyper-IL-6 solution or saline solution four hours prior to irradiation (17.5 Gy) directed at the head and neck. Salivary gland function was assessed two months after irradiation and compared to normal control rats.

The present invention provides methods for protecting against or treating toxicities associated with cancer therapy in a subject, the methods comprise administering to a subject in need of such treatment a pharmaceutical composition comprising a therapeutically effective amount of a polypeptide complex comprising human IL-6 and human sIL-6R or a fragment or analog thereof. The methods of the present invention are particularly useful in subjects undergoing ionizing radiation therapy or chemotherapy.

Among the toxicities associated with ionizing radiation therapy or chemotherapy is xerostomia. Thus, the present invention further provides methods for preventing or treating xerostomia caused by radiation therapy or chemotherapy comprising administering to a subject in need of such treatment a therapeutically effective amount of a pharmaceutical composition comprising as an active agent a polypeptide complex comprising human IL-6 and human sIL-6R, or a fragment or analog thereof.

The term "polypeptide complex comprising IL-6 and sIL-6R" refers both to a bimolecular polypeptide complex which features both the IL-6 polypeptide and the soluble IL-6 receptor (SIL-6R) polypeptide, and to a unimolecular polypeptide which includes IL-6 polypeptide and sIL-6R polypeptide, at any order. Preferably, the bioactive portions of sIL-6R and IL-6 are connected to each other directly or via a flexible linker substantially as previously described (see International Patent Application Publications Nos. WO 97/32891; WO 99/62534; WO 03/02981; Fischer, M., et al. Nat. Biotechnol. 15: 142-147, 1997; and Peters, M., J. Immunol. 161: 3575-3581, 1998, incorporated by reference as if fully set forth herein) as well as any biologically active analog or fragment thereof. The accession number for IL-6 is M14584 (GenBank Protein Sequences Database), and for the soluble IL-6 receptors is M57230, M20566, and X12830.

The term "biologically active analog" refers to any homologous polypeptide to IL-6 or sIL-6R, which includes any amino acid substitution, deletion, or addition, while retaining the biological activity of the original polypeptide. Thus, a polypeptide complex comprising an analog or fragment of IL-6 and/or an analog or fragment of sIL-6R should retain the capability to directly activate the membrane receptor for the IL-6/sIL-6R polypeptide complex known as gp130 or at least one component of the down-stream signaling cascade of gp130. The present invention encompasses fragments of IL-6 and sIL-6R so long as the fragments retain the biological activity of the native polypeptide.

The term "linker" relates to linkers of any kind, which are suitable for the binding of IL-6 with sIL-6R. Examples of such linkers include, but are not limited to, bifunctional, chemical cross-linkers, a disulfide-bridge connecting a first amino acid of IL-6 and a second amino acid of sIL-6R, a peptide or a polypeptide.

The unimolecular protein can be a fusion polypeptide. Thus, polypeptides featuring the bioactive portions of IL-6 and sIL-6R can be fused with each other and the linker can be a disulfide-bridge produced by the two polypeptides. Preferably, the linker is a peptide, which connects the two other polypeptides with each other. These fusion polypeptides can include human sIL-6R polypeptide (SEQ ID NO:2), which is the extracellular subunit of the human IL-6R and human IL-6-polypeptide (SEQ ID NO:1), whereby the sIL-6R and IL-6 are connected, at any order, by different peptide linkers with each other. According to a certain embodiment, the peptide linker has the amino acid sequence as set forth in SEQ ID NO:7.

The term "Hyper-IL-6" refers to a unimolecular protein as set forth in SEQ ID NO:3, which consists of amino acid residues 1-323 of human sIL-6R as set forth in SEQ ID NO:2 and amino acid residues 29-212 of human IL-6 as set forth in SEQ ID NO:4, connected with a flexible peptide linker as set forth in SEQ ID NO:7, substantially as described in International Patent Application Publication No. WO 97/32891 referred to as "H-IL-6" in that reference.

A polypeptide complex comprising of amino acids 113-323 of the sIL-6R polypeptide (SEQ ID NO:5) and amino acids 29-212 of the IL-6-polypeptide (SEQ ID NO:4) is also encompassed in the present invention. Also encompassed is a polypeptide complex comprising of amino acids 114-323 of the sIL-6R-polypeptide (SEQ ID NO:6) and amino acids 29-212 of the IL-6-polypeptide (SEQ ID NO:2). Other unimolecular complexes, bimolecular complexes, analogs, fragments, and combinations thereof are encompassed in the present invention so long as the complexes, analogs, fragments, and combinations thereof retain the capability to activate gp130 or any component of the down-stream signaling cascade of gp130.

By "peptide" it is meant that the peptide consists of not more than 50 amino acids. By "polypeptide" it is meant that the polypeptide generally consists of more than 50 amino acid residues.

By using "amino acid substitution", it is meant that functionally equivalent amino acid residues are substituted for residues within the sequence resulting in a silent change. For example, one or more amino acid residues within the polypeptide sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, non-conservative substitutions, wherein one amino acid within a polypeptide is substituted with an amino acid of a different polarity or hydrophobicity, are also included within the present invention so long as the polypeptide retains the original biological activity. The invention further encompasses polypeptides having one or more amino acids at the D-isomer configuration and polypeptides having one or more non-natural amino acids.

The term "non-natural amino acids" refers to an amino acid that is different from the twenty naturally occurring amino acids in its side chain functionality. The term "non-natural amino acid" includes, but is not limited to, amino acids which occur naturally by modification of a naturally encoded amino acid, but are not themselves incorporated into a growing polypeptide chain by the translation complex. Examples of amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of natural amino acids.

Thus, the present invention encompasses polypeptide analogs of which at least one amino acid has been modified. Modifications of amino acid residues include, but are not limited to, amidation, acylation, glycosylation, oxidation, permanent phosphorylation, reduction, myristylation, sulfation, acylation, acetylation, ADP-ribosylation, cyclization, disulfide bond formation, hydroxylation, iodination, methylation, derivatization by protecting/blocking groups, or any other derivatization method known in the art. Such modifications, which do not destroy, but maintain or improve the biological activity of the original polypeptide, can occur anywhere along the sequence of the analog including at the peptide backbone, at an amino acid side-chain, or at the amino or carboxyl termini.

The polypeptide complex comprising human IL-6 and sIL-6R of the present invention, analogs or fragments thereof can be produced by various methods known in the art, including isolation from natural sources, synthetic production or recombinant production.

The polypeptides of the invention can be isolated from natural sources including, but not limited to, blood and urine. The polypeptides can be produced by synthetic production. Synthetic production of polypeptides is well known in the art and is available commercially from a variety of companies. IL-6/sIL-6R polypeptide complexes can be synthesized using a standard direct peptide synthesis method (e.g., as summarized in Bodanszky, 1984, Principles of Peptide Synthesis, Springer-Verlag, Heidelberg) such as via solid-phase synthesis (see, e.g., Merrifield, 1963, J. Am. Chem. Soc. 85:2149-2154).

Included within the scope of the invention are chimeric or fusion proteins comprising IL-6 polypeptide, a fragment or analog thereof joined at its amino or carboxy-terminus or at one of the side chains via a peptide bond to an amino acid sequence of sIL-6R, or a fragment or analog thereof. Such fusion proteins can be made by protein synthesis, e.g., by use of a peptide synthesizer, or by ligating the appropriate nucleic acid sequences encoding the desired amino acid sequences to each other by methods known in the art, in the proper coding frame, and expressing the fusion protein by methods commonly known in the art.

Recombinant production can be achieved by the use of an isolated polynucleotide encoding IL-6 and sIL-6R, or an analog or fragment thereof, the isolated polynucleotide operably linked to a promoter for the expression of the polynucleotide. Optionally, a regulator of the promoter is added. The construct comprising the polynucleotide encoding the polypeptide or an analog or fragment thereof, the promoter, and optionally the regulator can be placed in a vector, such as a plasmid, virus or phage vector. The vector can be used to transfect or transform a host cell, e.g., a bacterial, yeast, insect, or mammalian cell.

The term "polynucleotide" means a polymer of deoxyribonucleic acid (DNA) or ribonucleic acid (RNA), which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

One who is skilled in the art will appreciate that more than one nucleic acid may encode any given protein in view of the degeneracy of the genetic code and the allowance of exceptions to classical base pairing in the third position of the codon, as given by the so-called "Wobble rules". Moreover, polynucleotides that include more or less nucleotides can result in the same or equivalent proteins. Accordingly, it is intended that the present invention encompasses all polynucleotides that encode the IL-6/sIL-6R polypeptides, preferably Hyper-IL-6.

The polynucleotides of the present invention can be expressed as a transported protein where the polypeptide is isolated from the medium in which the host cell containing the polynucleotide is grown, or may be expressed as an intracellular protein by deleting the leader or other peptides, in which case the polypeptide is isolated from the host cells. The polypeptide so isolated is then purified by protein purification methods known in the art.

The polypeptides of the invention can be provided to the tissue of interest by transferring to cells an expression vector comprising an isolated polynucleotide encoding the polypeptide of the invention. The cells produce and secrete the polypeptide such that it is suitably provided to cells of interest.

The expression vectors comprise a promoter. In the context of the present invention, the promoter must be able to drive the expression of the polynucleotide within the cells. Many viral promoters are appropriate for use in such an expression cassette including, but not limited to, retroviral ITRs, LTRs, immediate early viral promoters (IEp; such as herpes virus Iep, e.g., ICP4-IEp and ICP0-IEp and cytomegalovirus (CMV) IEp), late viral promoters, latency-active promoters (LAPs), Rous Sarcoma Virus (RSV) promoters, and Murine Leukemia Virus (MLV) promoters. Other suitable promoters are eukaryotic promoters, which contain enhancer sequences (e.g., the rabbit β-globin regulatory elements), constitutively active promoters (e.g., the β-actin promoter, human $\alpha_1$-antitrypsin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the polypeptide of the invention and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors must be introduced into the cells in a manner such that they are capable of expressing the isolated polynucleotide encoding the polypeptide of the invention contained therein. Any suitable vector can be so employed, many of which are known in the art. Examples of such vectors include naked DNA or RNA vectors (such as oligonucleotides or plasmids), viral vectors such as adeno-associated viral vectors (Berns et al., 1995, Ann. N.Y. Acad. Sci. 772: 95-104), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640), papilloma virus vectors, picornavirus vectors, polyoma virus vectors, retroviral vectors, SV40 viral vectors, vaccinia virus vectors, and other vectors known in the art. In addition to the expression vector of interest, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (see, e.g., Sambrook et al., 1989, Molecular Cloning: A Laboratory Manual, 2d edition, Cold Spring Harbor Press) and include direct cloning, site specific recombination using recombinases, homologous recombination, and other suitable methods of constructing a recombinant vector (see WO 2006/134601 to the applicant of the present invention, incorporated by reference as if fully set forth herein). In this manner, an expression vector can be constructed such that it can be replicated in any desired cell, expressed in any desired cell, and can even become integrated into the genome of any desired cell.

The expression vector comprising a polynucleotide encoding human IL-6 and human sIL-6R polypeptides, preferably Hyper-IL-6, is introduced into the cells by any means appropriate for the transfer of DNA into cells. Many such methods are well known in the art (Sambrook et al., supra; Watson et al., 1992, Recombinant DNA, Chapter 12, 2d edition, Scientific American Books. See also WO 2006/134601 ibid). For eukaryotic cells, vectors may be introduced through the use of, for example, electroporation, transfection such as hydrodynamics-based transfection, infection, DNA coated microprojectiles or protoplast fusion (see, for example, Liu, F. et al., 1999, Gene Ther. 6: 1258-1266).

Within the cells, the polynucleotide is expressed such that the cells express and secrete the polypeptide. Successful expression of the polynucleotide can be assessed using standard molecular biological techniques (e.g., Northern hybridization, Western blotting, immunoprecipitation, enzyme immunoassay, etc.). Reagents for detecting the expression of polynucleotides and the secretion of polypeptides from transfected cells are known in the art (see also examples herein below).

The polypeptide of the invention produced by recombinant techniques can be purified so that the polypeptide is substantially pure when administered to a subject. The term "substantially pure" refers to a compound, e.g., a protein or polypeptide, which has been separated from components, which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., by column chromatography, gel electrophoresis or HPLC analysis. A polypeptide is also substantially pure when it is essentially free of naturally associated components or when it is separated from the native contaminants, which accompany it in its natural state.

Pharmaceutical Compositions and Administration Routes

The present invention provides pharmaceutical compositions comprising as an active agent a polypeptide complex comprising human IL-6 and human sIL-6R or an analog or fragment thereof and a pharmaceutically acceptable carrier. The present invention further provides pharmaceutical compositions comprising as an active agent an isolated polynucleotide encoding the polypeptide of the invention, expression vector comprising the polynucleotide, or cells transfected with the expression vector, and a pharmaceutically acceptable carrier.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active agent is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The present invention includes pharmaceutically acceptable salts of the polypeptides. Pharmaceutically acceptable salts include those formed with free amino groups such as those derived from acetic, benzenesulfonic, benzoic, camphorsulfonic, citric, ethanesulfonic, fumaric, gluconic, glutamic, hydrobromic, hydrochloric, isothionic, lactic, maleic, malic, mandelic, methanesulfonic, mucic, nitric, oxalic, pamoic, pantothenic, phosphoric, succinic, sulfuric, tartaric, p-toluenesulfonic acid, and the like, and those formed with free carboxyl groups such as those derived from aluminum, ammonium, calcium, copper, ferric, ferrous, lithium, magnesium, manganic salts, manganous, potassium, sodium, zinc, primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compositions can take the form of solutions, suspensions, emulsions, tablets, capsules, powders, suppositories, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the active agent of the invention, preferably in a substantially purified form, together with a suitable amount of carrier so as to provide the form for proper administration to the subject.

The amount of a polypeptide of the invention or an isolated polynucleotide encoding the polypeptide or an expression vector comprising the isolated polynucleotide encoding said polypeptide or cells expressing the polypeptide, which will be effective in the prevention or treatment of said toxicities will depend on the nature of the toxicity, and can be determined by standard clinical techniques. For example, in vitro assays can optionally be employed to help identifying optimal dosage ranges. Alternatively or additionally, in vivo assays with animal models can be performed to determine optimal dosage ranges (see the example herein below). The precise dose to be employed in the formulation will also depend on the route of administration, and the seriousness of the toxicity, and should be decided according to the judgment of the practitioner and each patient's circumstances. Effective doses may be extrapolated from dose-response curves derived from in vitro or animal model test bioassays or systems.

A composition comprising a source of a polypeptide of the invention (i.e., an IL-6/sIL-6R polypeptide complex, or an isolated polynucleotide encoding the polypeptide, or an expression vector comprising the isolated polynucleotide encoding said polypeptide, or cells expressing the polypeptide, as described herein above) can be introduced into the systemic circulation, which will distribute the source of the polypeptide to the injured tissue where toxicity occurred. Alternatively, a composition containing a source of the polypeptide can be applied locally to the injured tissue where toxicity occurs (e.g., by injection or as a bolus within the tissue).

Methods of introduction of a pharmaceutical composition comprising a source of a polypeptide of the invention into a subject include, but are not limited to, direct administration into or in the vicinity of a damaged tissue, topical, intradermal, transdermal, intramuscular, intraperitoneal, intravenous, subcutaneous, intranasal, epidural, and oral administration.

The compounds can be administered by any convenient route, for example by infusion or bolus injection, by absorption through epithelial linings (e.g., oral mucosa, rectal and intestinal mucosa, etc.), and can be administered together with other therapeutically active agents. The administration can be localized such as into the parotid or submandibular glands, or it can be systemic.

It may be desirable to administer the pharmaceutical composition of the invention locally to the injured tissue in need of treatment; this can be achieved by, for example, and not by way of limitation, local infusion, topical application, e.g., in conjunction with a wound dressing, by injection, by means of a catheter, or by means of an implant, said implant being of a porous, non-porous, or gelatinous material. According to some embodiments, administration can be by direct injection e.g., via a syringe, at the site of the injured tissue where toxicity occurred or by intravenous infusion.

According to some embodiments, a source of a polypeptide of the invention can be applied to the skin. The carrier can be in the form of, for example, and not by way of limitation, an ointment, cream, gel, paste, foam, aerosol, suppository, pad or gelled stick.

For directed internal applications, the pharmaceutical composition can be in the form of tablets or capsules, which can contain any of the following ingredients or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to the components listed above, a liquid carrier such as fatty oil. In addition, dosage unit forms can contain various other materials which modify the physical form of the dosage unit, for example, coatings of sugar, shellac, or other enteric agents.

A polypeptide of the invention can be delivered in a controlled release system. In one embodiment, an infusion pump can be used to administer the polypeptide. Alternatively, the polypeptide of the invention can be administered in combination with a biodegradable, biocompatible polymeric implant, which releases the polypeptide over a controlled period of time at the injured tissue. Examples of preferred polymeric materials include polyanhydrides, polyorthoesters, polyglycolic acid, polylactic acid, polyethylene vinyl acetate, copolymers and blends thereof (see Medical applications of controlled release, Langer and Wise (eds.), 1974, CRC Pres., Boca Raton, Fla.).

Uses of the Compositions

Treatment of tumors with ionizing radiation (hereinafter referred to also as "cancer radiotherapy") is used extensively in cancer therapy. The goal of such treatment is to elicit the destruction of tumor cells and to inhibit tumor cell growth presumably through DNA damage, while causing minimum damage to non-tumor cells and tissues. Collateral damage to adjacent tissues often limits the effectiveness of radiotherapy of certain tumors, such as brain tumors and tumors in the abdominal cavity and the neck.

The dominant consideration in determining radiation doses for cancer radiotherapy is the assessment of tolerance of the most radiosensitive normal tissues/organs in the treatment field. The problem is that late adverse reactions develop at various time points following termination of irradiation in the adjacent tissues. These adverse effects are the result of some tissue damage caused by radiation to the adjacent tissues. This damage is suggested to be associated with release of inflammation-inducing cytokines which progressively exacerbate the initial damage.

The present invention provides a method for protecting against, preventing or treating toxicity associated with ionizing radiation comprising administering to a subject in need of such treatment a therapeutically effective amount of a pharmaceutical composition comprising as an active agent a source of a polypeptide of the invention and a pharmaceutically acceptable carrier. The source of a polypeptide according to the present invention refers to a polypeptide complex comprising human IL-6 or an analog or fragment thereof and human sIL-6R or an analog or fragment thereof according to the principles of the present invention; an isolated polynucleotide encoding the polypeptide of the invention; an expression vector comprising the isolated polynucleotide encoding the polypeptide of the invention; and a host cell transfected with an expression vector comprising an isolated polynucleotide encoding the polypeptide of the invention.

Many of the normal tissues which are adversely affected by ionizing radiation such as the skin, oral mucosa, esophageal mucosa, rectal mucosa, vaginal mucosa and bladder epithelium can be protected from the acute and chronic effects which develop post irradiation.

Thus, administration of the pharmaceutical compositions of the present invention enable the use of higher radiation doses, as it offers a method to manage more severe post irradiation complications and can effectively limit their magnitude.

The present invention further provides a method for protecting against, preventing or treating toxicity associated with chemotherapy comprising administering to a subject in need of such treatment a therapeutically effective amount of a pharmaceutical composition comprising as an active agent a source of the polypeptide of the invention and a pharmaceutically acceptable carrier.

The terms "treating", "treat" or "treatment" as used herein include preventative (e.g., prophylactic), palliative and curative treatment. Thus, the methods of the present invention are useful for improving tissue function in a subject having, or at risk of, tissue toxicity. According to one embodiment, the subject is a mammal. According to another embodiment, the mammal is a human.

The term "therapeutically effective amount" means an amount effective to treat or prevent tissue injury or damage, without undue adverse physiological effects or side effects.

As used herein, the term "toxicity" means a disorder characterized by a recognized etiologic agent or agents, an identifiable group of signs and symptoms, including adverse effects, unwanted effects, undesired effects, or abnormal signs or symptoms or consistent anatomical alterations.

In some embodiments, the methods of the invention are used to treat toxicities associated with ionizing radiation. The term "ionizing radiation" as used herein refers to photons having enough energy to ionize a bond, such as, $\alpha$, $\beta$ and $\gamma$ rays from radioactive nuclei and x-rays. Other types of radiation, which may damage normal tissues while irradiating the tumor tissue, are laser irradiation, microwave irradiation, ultraviolet radiation, infrared radiation or ultrasonic thermotherapy; all are encompassed in the present invention. The applied radiation may be used locally, to a specific organ or tissue or it may be a total body radiation.

In other embodiments, the methods of the invention are used to treat toxicities associated with administration of a chemotherapeutic agent.

Examples of chemotherapeutic agents include, but not limited to, taxanes such as paclitaxel and docetaxel; alkylating agents which include nitrogen mustards such as mechlorethamine, cyclophosphamide, ifosamide, melphalan (phenalphenine mustard) and chlorambucil; ethylenimines and methylmelamines such as altretamine, diaziquone (AZQ) and thiotepa; alkyl sulfonates such as busulfan; nitrosoureas such as carmustine (BCNU), lomustine (CCNU), semustine (methyl-CCNU) and streptozocin (streptozotocin); and triazenes such as dacarbazine (DTIC; dimethyltriazenoimidazolecarboxamide); anti metabolites, which include folic acid analogs such as methotrexate, trimetrexate and other dihydrofolates; pyrimidine analogs such as fluorouracil (5-fluorouracil; 5-FU), floxuridine (fluorodeoxyuridine; FUdR) and cytarabine (cytosine arabinoside); purine analogs and related inhibitors such as mercaptopurine (6-mercaptopurine; 6-MP), thioguanine (6-thioguanine; TG) and pentostatin (2'-deoxycoformycin); natural products, which include vinca alkaloids such as vinblastine, vincristine, navelbine and vincristine; epipodophylotoxins such as etoposide and teniposide; antibiotics such as dactinomycin (actinomycin D), daunorubicin (daunomycin; rubidomycin); doxorubicin, bleomycin, plicamycin (mithramycin) and mitomycin (mitomycin C); enzymes such as L-asparaginase; and biological response modifiers such as interferon-α and other interferons; platinum coordination complexes such as cisplatin (cis-DDP), carboplatin and oxaliplatin; anthracenediones such as mitoxantrone; substituted ureas such as hydroxyurea; methylhydrazide derivatives such as procarbazine (N-methylhydrazine, MIH), and adrenocortical suppressants such as mitotane (o,p'-DDD) and aminoglutethimide; hormones and antagonists which include adrenocorticosteroids such as prednisone; progestins such as hydroxyprogesterone caproate, medroxy progesterone acetate and megestrol acetate; estrogens such as diethylstilbestrol and ethinyl estradiol; antiestrogens such as tamoxifen; androgens such as testosterone propionate and fluoxymetsterone; antiandrogens such as flutamide; and gonadotropin-releasing hormone analogs such as leuprolide; camptothecins such as irinotecan, topotecan; gemciatdins such as gemcitabine; estramustine phosphate, VM-26 (vumon) and all-trans retinoic acid (ATRA). These agents are normally used in the treatment of head and neck, ovarian, breast, colon, lung, prostate, testicular and cervical cancers, as well as in certain lymphomas, leukemias, and cancers of the CNS.

The toxicities associated with the administration of chemotherapeutic agents or radiation therapy include, but are not limited to xerostomia, mucositis, neurotoxicity, ototoxicity, pulmonary toxicity, cytopenia, myelosuppression, cardiotoxicity, alopecia, infertility and local inflammation from extravasation into the skin. According to a currently exemplary embodiment, the toxicity is xerostomia.

The term "xerostomia" as used herein means dryness of mouth due to salivary gland dysfunction. Typically, xerostomia is induced by radiation. The term "acute xerostomia" as used herein means xerostomia occurring within 90 days of treatment initiation, characterized by dryness of mouth with thick, sticky saliva, altered taste, or acute salivary glands necrosis. The term "late xerostomia" as used herein means xerostomia occurring 90 days to 2 years after treatment initiation, characterized by dryness, poor saliva production, or fibrosis of salivary glands.

The term "mucositis" as used herein means inflammation of mucosal membranes lining the digestive tract induced by radiation or chemotherapy. The present invention encompasses acute mucositis and chronic mucositis. The term "acute mucositis" as used herein means mucositis occurring within 90 days of treatment initiation, characterized by parchy or confluent pseudomembranes, ulceration, or necrosis.

The term "late mucositis" as used herein means mucositis occurring 90 days to 2 years after treatment initiation, characterized by mucosal atrophy, dryness, telangiectasia or ulceration.

The term "neurotoxicity" as used herein refers to loss or distortion of sensation in the fingers, toes, hands and feet, as well as loss of fine muscle movements, resulting in the inability to perform routine functions such as buttoning of clothes. In more severe cases, neurotoxicity is manifested by loss of sufficient motor function so that the patient requires walkers or wheelchairs.

The term "ototoxicity" as used herein means tinnitus and/or hearing loss in the high frequency range (4000-8000 Hz). Ototoxicity may also be manifested by decreased ability to hear normal conversational tones, and even by deafness. Hearing loss can be unilateral or bilateral and tends to become more frequent and severe with repeated treatments.

As ionizing radiation often results in chronic toxicities which can develop months or years after irradiation, the present invention also encompasses late damages or toxicities. Examples of late toxicities include, but are not limited to, fibrosis and vasculopathy. Thus, for example, a well recognized complication of pelvic field radiation therapy is proctitis, with a frequency between 5% and 20%. Manifestations include tenesmus, bleeding, diarrhea, and fecal incontinence. The proctitis is mostly due to the vasculopathy which may appear as late as one year or more after the exposure to pelvic irradiation. Irradiation of brain tumors is associated with long term complications of radiation therapy such as encephalopathy and vasculopathy of the arteries. Lung cancer is relatively resistant to radiation and radiation pneumonitis is a major obstacle to increasing the radiation dose. Exposure of the lungs to ionizing radiation induces pneumonitis as an acute phase which subsides after a few weeks, and followed by inflammation and fibrosis as the chronic phase that can develop months or years after irradiation. Thus, the present invention provides methods for preventing or treating toxicities such as fibrosis and vasculopathy resulting from exposure to ionizing radiation following irradiation treatment of cancers.

The pharmaceutical compositions of the present invention can thus be used to prevent or treat fibrosis caused by radiotherapy or chemotherapy of various types of cancers and their metastases, including, but without being limited to, breast carcinoma, lung carcinoma, squamous cell carcinoma, basal cell carcinoma, melanoma, Kaposi sarcoma, prostate carcinoma, hemangioma, meningioma, astrocytoma, neuroblastoma, carcinoma of the pancreas, gastric carcinoma, colorectal carcinoma, colon carcinoma, transitional cell carcinoma of the bladder, carcinoma of the larynx, chronic myeloid leukemia, acute lymphocytic leukemia, acute promyelocytic leukemia, multiple myeloma, T-cell lymphoma, B-cell lymphomas, gallbladder, bronchial and skin cancers. According to certain embodiments, the pharmaceutical compositions of the present invention can be used to prevent or treat fibrosis caused by radiotherapy to mouth cancer, lung cancer, prostate cancer, brain cancer and skin cancer.

Other conditions which can be treated by radiation include psoriasis and intraocular inflammation (caused for example by laser irradiation).

The pharmaceutical composition of the invention can be administered prior to, simultaneously, and/or subsequently to the administration of a chemotherapeutic agent and/or radiation therapy. According to some embodiments, the pharmaceutical composition is administered no more than 24 hours prior to the administration of ionizing radiation or a chemotherapeutic agent. According to other embodiments, the pharmaceutical composition is administered no more than 12 hours prior to the administration of ionizing radiation or a chemotherapeutic agent. According to additional embodiments, the pharmaceutical composition is administered no more than 4 hours prior to the administration of ionizing radiation or a chemotherapeutic agent. According to additional embodiments, the pharmaceutical composition is administered no more than 1 hour prior to the administration of ionizing radiation or a chemotherapeutic agent.

The source of the polypeptide of the present invention can be administered alone or in conjunction with other therapeutic agents.

EXAMPLE 1

Effect of Hyper-IL-6 on Radiation-Induced Xerostomia in Rats

Animals

Male Sabra rats (200-230 gr) were purchased from Harlan (Israel) and maintained in a central animal facility under SPF conditions, at a temperature of ~23° C. in a 12-hour light-dark cycle. The rats received commercial rodent chow and water ad libitum and were acclimated for at least 5 days prior to use. All treatment protocols were approved by the Institutional Animal Care and Use Committee. Hyper-IL-6 (50 ng) or saline solution (control group) each was infused in a volume of 50 µl per submandibular gland to anesthetized rats four hours prior to irradiation via cannulation of the gland with tapered polyethylene tubing (PE 10). Irradiation was performed on anesthetized rats that were placed on their backs exposing only their head and neck region. To prevent exposure of other organs to the radiation the rest of the body was shielded with a perspex body shield. A wax layer 1 cm thick is placed on the area to be irradiated to ensure homogenous dosing. Irradiation was performed with a single exposure of 17.5 Gy, in a field 32×5 cm, radiation rate 600 machine units/min, the distance between the irradiation source and the target (SSD) 90 cm (CLINAC 6, x-ray radiation). Control rats were sham irradiated.

Analysis of Salivary Gland Function

Measuring salivary gland fluid output was assessed 8 weeks post irradiation. Anaesthetized rats were tracheotomized and the main excretory ducts of the submandibular glands cannulated with tapered polyethylene tubing (PE 10). Saliva was collected separately from each gland for 20 minutes following pilocarpine (5 mg/Kg, s.c.) stimulation via injection.

Recombinant Hyper-IL-6 Protein

Hyper-IL-6 is a protein complex consisting of human IL-6 covalently attached by a flexible peptide linker to the soluble IL-6R (sIL-6R) as defined by European Patent EP-B1 0 888 384. Recombinant Hyper-IL-6 protein was prepared from culture supernatants of genetically engineered Chinese Hamster Ovary (CHO) cells carrying a HIL-6 gene cassette. HIL-6 was purified from supernatants by anion-exchange chromatography and gel filtrations, and then visualized by sodium dodecyl sulfate-polyacrylamide gel electrophoresis and silver staining (Peters et al. J. Immunol. 161: 3575-3581, 1998).

Statistical Analysis

Statistical comparison of means was performed by One-way Analysis of Variance (ANOVA) using GraphPad InStat® software. $P \leq 0.05$ is considered significant.

Results

Analysis of salivary gland function two months after radiation exposure as measured by salivary gland fluid output revealed that irradiation at 17.5 Gy induced a 37% reduction in salivary gland function (FIG. 1). In contrast, rats pretreated with Hyper-IL-6 displayed only a 10% reduction in salivary gland function (FIG. 1). Similar findings were observed in two independent experiments. These results demonstrate that treatment of salivary glands with Hyper-IL-6 prior to irradiation renders nearly complete protection from injury and maintains gland function. Thus, treatment of salivary glands with Hyper-IL-6 prior to exposure to ionizing radiation is useful for the prevention of xerostomia in rats.

EXAMPLE 2

Effect of Hyper-IL-6 on Radiation-Induced Xerostomia in Mice

Animals

Female C3H mice (5-6 Weeks old, 8-19 grams) were purchased from Harlan (Israel) and maintained in a central animal facility under SPF conditions, at a temperature of ~23° C. in a 12-hour light-dark cycle. The mice received commercial rodent chow and water ad libitum and were acclimated for at least 5 days prior to use. All treatment protocols were approved by the Institutional Animal Care and Use Committee. Hyper-IL-6 (50-100 ng) or saline solution was infused in a volume of 50 µl per submandibular gland to anesthetized mice three to four hours prior to irradiation via canulation of the gland with tapered polyethylene tubing (PE 10). Irradiation (15 Gy) to the head and neck region was performed on mice without anesthesia placed in a perspex holding chamber. Irradiation was performed with a single exposure of 15 Gy, in a field 32×6 cm, at a radiation rate of 600 mGy/min, SSD 100 cm (CLINAC 6, of x-ray radiation).

Results

Figure 2A:
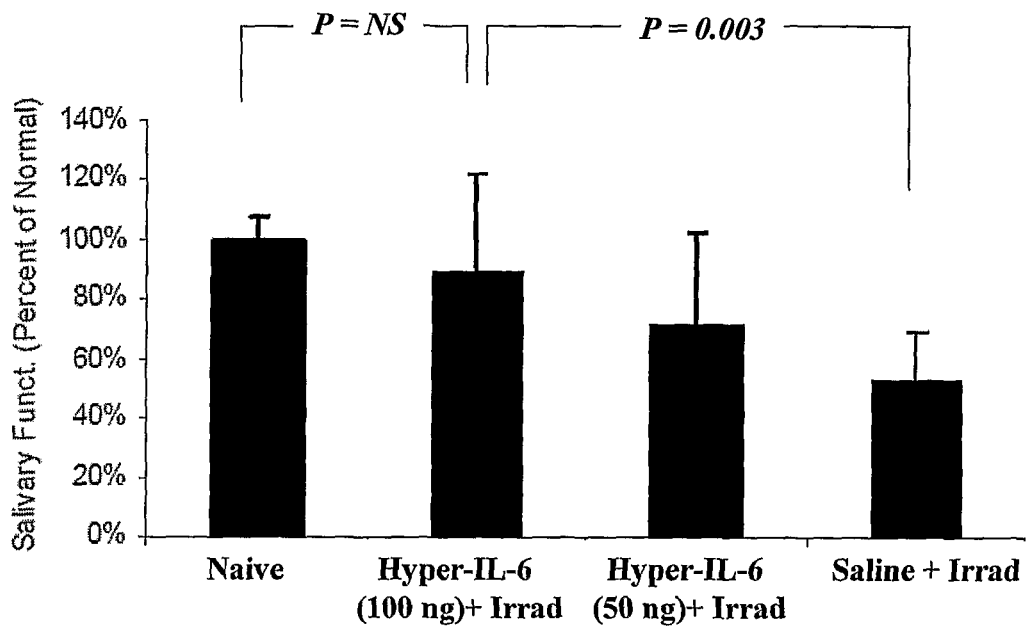
FIG. 2 shows the effect of Hyper-IL-6 on irradiation-induced xerostomia in mice. Female C3H mice were infused in the submandibular gland with either Hyper-IL-6 solution or saline solution four hours prior to irradiation (15 Gy) directed at the head and neck. Salivary gland function (FIG. 2A) and average body weight (FIG. 2B) were assessed two months after irradiation and compared to normal mice.
Figure 2B:
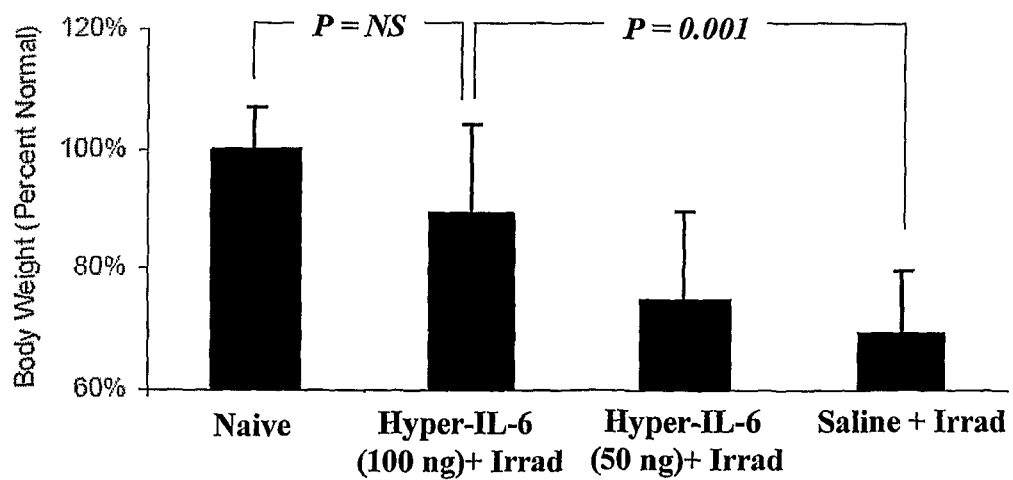

Salivary gland function and body weight were assessed two month after radiation exposure and compared to naive control mice. The experiment revealed that irradiation at 17.5 Gy induced a 48% reduction in salivary gland function (FIG. 2A) and 31% reduction in body weight (FIG. 2B). In contrast, mice pre-treated with 50 or 100 ng of Hyper-IL-6 displayed only a 30% and 12% reduction in salivary gland function, respectively (FIG. 2A), and 27% and 11% reduction in body weight, respectively (FIG. 2B). Similar findings were observed in two independent experiments. These results demonstrate that treatment of salivary glands with Hyper-IL-6 prior to irradiation renders nearly complete protection from injury and maintains gland function. Thus, treatment of salivary glands with Hyper-IL-6 prior to exposure to ionizing radiation is useful for the prevention of xerostomia in mice.

Cancer therapies including radiation and chemotherapy often result in the indiscriminate injury of healthy tissues, leading to undesirable side effects of a temporary or even permanent nature, and effectively limiting the applicable dose of a therapeutic agent. Topical or limited exposure of these tissues to Hyper-IL-6 prior to treatment with radiation or chemotherapeutic agents are thus useful for preventing or limiting the extent of injury to normal, healthy tissues, thereby improving the patient's quality of life, while extending the permissible dosage of a given therapeutic agent to the tumor.

EXAMPLE 3

The Effect of Hyper-IL-6 on the Induction of Signal Transduction Mediated by STAT3, ERK and AKT The effect of Hyper-IL-6 on the induction of signal transduction mediated by STAT3, ERK and AKT was studied in mice. Salivary glands from female C3H mice were infused with either Hyper-IL-6 (100 ng) or saline solution via a canula to the submandibular salivary glands in a volume of 20, 35, or 50 Salivary glands were removed 60 minutes later and protein extracts were analyzed for pSTAT3, pERK, and pAKT proteins by Western blot analysis.

Western Blot Analysis of pSTAT3, pERK1/2 and pAKT

Protein extracts were prepared from tissue samples (~50 mg) by homogenization in 0.5 ml whole cell lysis buffer (1% NP-40, 10 mM Tris pH 7.8, 150 mM NaCl, 40 mM EDTA, 10 mM Na-Pyrophosphate, 10 mM NaF, 1 mM PMSF, 4 mM Orthovanadate, Pepstatin A 1 µg/ml, Leupeptin 2 µg/ml). Protein extracts (50 µg) were separated by polyacrylamide gel electrophoresis and subjected to Western blot analysis. Western blots were probed with anti-pSTAT3 mouse mAb (Santa Cruz Biotechnology, Santa Cruz, Calif.), anti-pERK1/2 mouse mAb (Sigma) or anti-pAKT rabbit mAb (Cell Signaling, Danvers, Mass.), and anti-mouse HRP polymer or anti-rabbit HRP polymer (DAKO), respectively. The blots were developed using the ECL-Plus Western blotting Detection System (Amersham). As a loading control, the blots were stripped with 0.1 M glycine pH 2.8 and re-probed with a monoclonal anti-β-actin antibody, clone AC-74 (Sigma) and developed with HRP Envision (DAKO).

Results

Figure 3:
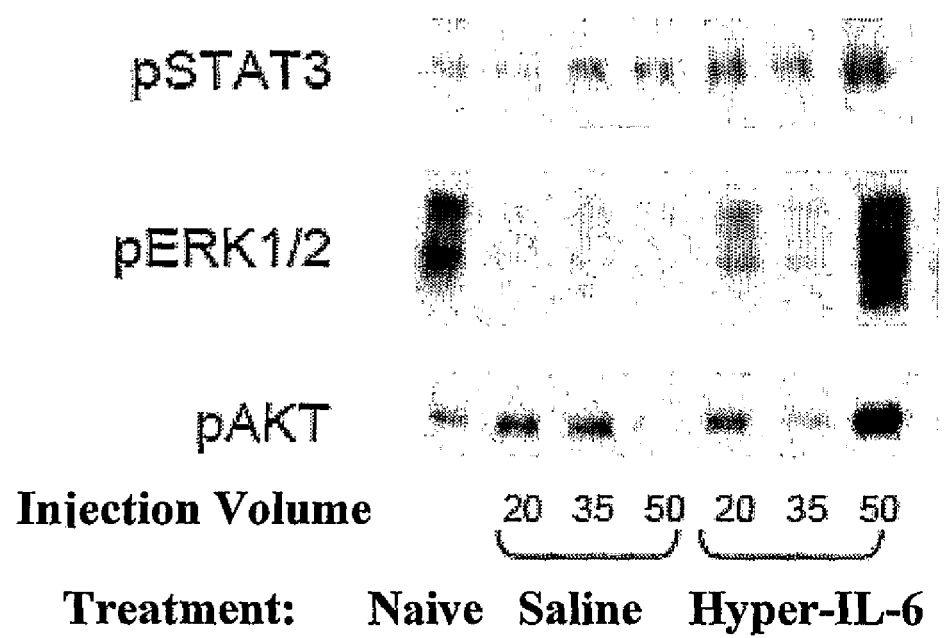
FIG. 3 shows the effect of Hyper-IL-6 on the phosphorylation of STAT3, ERK and AKT as measured by western blot analysis.

FIG. 3 shows that the Hyper-IL-6 induced signal transduction mediated by STAT3, ERK, and AKT is in part affected by infusion volume. Hyper-IL-6 infusion activated STAT3, ERK1/2 and AKT in the salivary glands and it was most efficient using a volume of 50 µl per gland.

It will be appreciated by persons skilled in the art that the present invention is not limited by what has been particularly shown and described herein above. Rather the scope of the invention is defined by the claims that follow.

The invention claimed is:

1. A method for preventing a toxicity associated with ionizing radiation in a subject comprising administering to a subject in need of such treatment a therapeutically effective amount of a pharmaceutical composition comprising as an active agent a polypeptide complex, and a pharmaceutically acceptable carrier, wherein the polypeptide complex is Hyper-IL-6 as set forth in SEQ ID NO:3, and wherein the toxicity is xerostomia.

2. The method according to claim 1, wherein the xerostomia is acute xerostomia.

3. The method according to claim 1, wherein the route of administering the pharmaceutical composition is selected from the group consisting of direct administration into or in the vicinity of a tissue having said toxicity, intramuscular, intraperitoneal, intravenous, subcutaneous, and epidural.

4. The method according to claim 1, wherein the pharmaceutical composition is formulated in a form selected from the group consisting of solutions, suspensions, emulsions, powders, and sustained-release formulations.

5. The method according to claim 1, wherein the pharmaceutical composition is administered prior to or simultaneously with exposure of the subject to ionizing radiation.

* * * * *

SEQUENCE LISTING

<160> NUMBER OF SEQ ID NOS: 8

<210> SEQ ID NO 1
<211> LENGTH: 212
<212> TYPE: PRT
<213> ORGANISM: Homo sapiens

<400> SEQUENCE: 1

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 2
<211> LENGTH: 323
<212> TYPE: PRT

<213> ORGANISM: Homo sapiens

<400> SEQUENCE: 2

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala

<210> SEQ ID NO 3
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 3

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg

```
                 20                  25                  30
Gly Val Leu Thr Ser Leu Pro Gly Asp Ser Val Thr Leu Thr Cys Pro
             35                  40                  45
Gly Val Glu Pro Glu Asp Asn Ala Thr Val His Trp Val Leu Arg Lys
 50                  55                  60
Pro Ala Ala Gly Ser His Pro Ser Arg Trp Ala Gly Met Gly Arg Arg
 65                  70                  75                  80
Leu Leu Leu Arg Ser Val Gln Leu His Asp Ser Gly Asn Tyr Ser Cys
                 85                  90                  95
Tyr Arg Ala Gly Arg Pro Ala Gly Thr Val His Leu Leu Val Asp Val
            100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
            130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
            195                 200                 205
Gln Gly Cys Gly Ile Leu Gln Pro Asp Pro Pro Ala Asn Ile Thr Val
            210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
            275                 280                 285
Val Val Gln Leu Arg Ala Gln Glu Glu Phe Gly Gln Gly Glu Trp Ser
            290                 295                 300
Glu Trp Ser Pro Glu Ala Met Gly Thr Pro Trp Thr Glu Ser Arg Ser
305                 310                 315                 320
Pro Pro Ala Arg Gly Gly Gly Ser Gly Gly Gly Ser Val Glu
            325                 330                 335
Pro Val Pro Pro Gly Glu Asp Ser Lys Asp Val Ala Ala Pro His Arg
            340                 345                 350
Gln Pro Leu Thr Ser Ser Glu Arg Ile Asp Lys Gln Ile Arg Tyr Ile
            355                 360                 365
Leu Asp Gly Ile Ser Ala Leu Arg Lys Glu Thr Cys Asn Lys Ser Asn
            370                 375                 380
Met Cys Glu Ser Ser Lys Glu Ala Leu Ala Glu Asn Asn Leu Asn Leu
385                 390                 395                 400
Pro Lys Met Ala Glu Lys Asp Gly Cys Phe Gln Ser Gly Phe Asn Glu
            405                 410                 415
Glu Thr Cys Leu Val Lys Ile Ile Thr Gly Leu Leu Glu Phe Glu Val
            420                 425                 430
Tyr Leu Glu Tyr Leu Gln Asn Arg Phe Glu Ser Ser Glu Glu Gln Ala
            435                 440                 445
```

```
Arg Ala Val Gln Met Ser Thr Lys Val Leu Ile Gln Phe Leu Gln Lys
    450                 455                 460

Lys Ala Lys Asn Leu Asp Ala Ile Thr Thr Pro Asp Pro Thr Thr Asn
465                 470                 475                 480

Ala Ser Leu Leu Thr Lys Leu Gln Ala Gln Asn Gln Trp Leu Gln Asp
                485                 490                 495

Met Thr Thr His Leu Ile Leu Arg Ser Phe Lys Glu Phe Leu Gln Ser
            500                 505                 510

Ser Leu Arg Ala Leu Arg Gln Met
        515                 520
```

<210> SEQ ID NO 4
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 4

```
Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Tyr Ile
                20                  25                  30

Leu Asp Gly Ile Ser Ala Leu Arg Lys Glu Thr Cys Asn Lys Ser Asn
            35                  40                  45

Met Cys Glu Ser Ser Lys Glu Ala Leu Ala Glu Asn Asn Leu Asn Leu
        50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
                100                 105                 110

Arg Ala Val Gln Met Ser Thr Lys Val Leu Ile Gln Phe Leu Gln Lys
            115                 120                 125

Lys Ala Lys Asn Leu Asp Ala Ile Thr Thr Pro Asp Pro Thr Thr Asn
    130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180
```

<210> SEQ ID NO 5
<211> LENGTH: 211
<212> TYPE: PRT
<213> ORGANISM: Artificial Sequence
<220> FEATURE:
<223> OTHER INFORMATION: Synthetic polypeptide

<400> SEQUENCE: 5

```
Pro Pro Glu Glu Pro Gln Leu Ser Cys Phe Arg Lys Ser Pro Leu Ser
1               5                   10                  15

Asn Val Val Cys Glu Trp Gly Pro Arg Ser Thr Pro Ser Leu Thr Thr
                20                  25                  30

Lys Ala Val Leu Leu Val Arg Lys Phe Gln Asn Ser Pro Ala Glu Asp
            35                  40                  45
```

```
Phe Gln Glu Pro Cys Gln Tyr Ser Gln Glu Ser Gln Lys Phe Ser Cys
         50                  55                  60

Gln Leu Ala Val Pro Glu Gly Asp Ser Ser Phe Tyr Ile Val Ser Met
 65                  70                  75                  80

Cys Val Ala Ser Ser Val Gly Ser Lys Phe Ser Lys Thr Gln Thr Phe
                 85                  90                  95

Gln Gly Cys Gly Ile Leu Gln Pro Asp Pro Pro Ala Asn Ile Thr Val
            100                 105                 110

Thr Ala Val Ala Arg Asn Pro Arg Trp Leu Ser Val Thr Trp Gln Asp
            115                 120                 125

Pro His Ser Trp Asn Ser Phe Tyr Arg Leu Arg Phe Glu Leu Arg
        130                 135                 140

Tyr Arg Ala Glu Arg Ser Lys Thr Phe Thr Thr Trp Met Val Lys Asp
145                 150                 155                 160

Leu Gln His His Cys Val Ile His Asp Ala Trp Ser Gly Leu Arg His
                165                 170                 175

Val Val Gln Leu Arg Ala Gln Glu Glu Phe Gly Gln Gly Glu Trp Ser
            180                 185                 190

Glu Trp Ser Pro Glu Ala Met Gly Thr Pro Trp Thr Glu Ser Arg Ser
        195                 200                 205

Pro Pro Ala
    210

<210> SEQ ID NO 6
<211> LENGTH: 210
<212> TYPE: PRT
<213> ORGANISM: Artificial Sequence
<220> FEATURE:
<223> OTHER INFORMATION: Synthetic polypeptide

<400> SEQUENCE: 6

Pro Glu Glu Pro Gln Leu Ser Cys Phe Arg Lys Ser Pro Leu Ser Asn
 1               5                  10                  15

Val Val Cys Glu Trp Gly Pro Arg Ser Thr Pro Ser Leu Thr Thr Lys
                 20                  25                  30

Ala Val Leu Leu Val Arg Lys Phe Gln Asn Ser Pro Ala Glu Asp Phe
             35                  40                  45

Gln Glu Pro Cys Gln Tyr Ser Gln Glu Ser Gln Lys Phe Ser Cys Gln
         50                  55                  60

Leu Ala Val Pro Glu Gly Asp Ser Ser Phe Tyr Ile Val Ser Met Cys
 65                  70                  75                  80

Val Ala Ser Ser Val Gly Ser Lys Phe Ser Lys Thr Gln Thr Phe Gln
                 85                  90                  95

Gly Cys Gly Ile Leu Gln Pro Asp Pro Pro Ala Asn Ile Thr Val Thr
            100                 105                 110

Ala Val Ala Arg Asn Pro Arg Trp Leu Ser Val Thr Trp Gln Asp Pro
            115                 120                 125

His Ser Trp Asn Ser Phe Tyr Arg Leu Arg Phe Glu Leu Arg Tyr
        130                 135                 140

Arg Ala Glu Arg Ser Lys Thr Phe Thr Thr Trp Met Val Lys Asp Leu
145                 150                 155                 160

Gln His His Cys Val Ile His Asp Ala Trp Ser Gly Leu Arg His Val
                165                 170                 175

Val Gln Leu Arg Ala Gln Glu Glu Phe Gly Gln Gly Glu Trp Ser Glu
            180                 185                 190

Trp Ser Pro Glu Ala Met Gly Thr Pro Trp Thr Glu Ser Arg Ser Pro
```

Pro Ala
    210

<210> SEQ ID NO 7
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 7

Arg Gly Gly Gly Gly Ser Gly Gly Gly Gly Ser Val Glu
1               5                   10

<210> SEQ ID NO 8
<211> LENGTH: 1560
<212> TYPE: DNA
<213> ORGANISM: Artificial Sequence
<220> FEATURE:
<223> OTHER INFORMATION: Synthetic polynucleotide

<400> SEQUENCE: 8

| | |
|---|---|
| atgctggccg tcggctgcgc gctgctggct gccctgctgg ccgcgccggg agcggcgctg | 60 |
| gccccaaggc gctgccctgc gcaggaggtg caagaggcg tgctgaccag tctgccagga | 120 |
| gacagcgtga ctctgacctg cccgggggta gagccggaag acaatgccac tgttcactgg | 180 |
| gtgctcagga agccggctgc aggctccac cccagcagat gggctggcat gggaaggagg | 240 |
| ctgctgctga ggtcggtgca gctccacgac tctggaaact attcatgcta ccgggccggc | 300 |
| cgcccagctg gactgtgca cttgctggtg gatgttcccc ccgaggagcc ccagctctcc | 360 |
| tgcttccgga gagccccct cagcaatgtt gtttgtgagt ggggtcctcg gagcacccca | 420 |
| tccctgacga caaaggctgt gctcttggtg aggaagtttc agaacagtcc ggccgaagac | 480 |
| ttccaggagc cgtgccagta ttcccaggag tcccagaagt tctcctgcca gttagcagtc | 540 |
| ccggagggag acagctcttt ctacatagtg tccatgtgcg tcgccagtag tgtcgggagc | 600 |
| aagttcagca aaactcaaac cttttcagggt tgtggaatct gcagcctga tccgcctgcc | 660 |
| aacatcacag tcactgccgt ggccagaaac ccccgctggc tcagtgtcac ctggcaagac | 720 |
| ccccactcct ggaactcatc tttctacaga ctacggtttg agctcagata tcgggctgaa | 780 |
| cggtcaaaga cattcacaac atggatggtc aaggacctcc agcatcactg tgtcatccac | 840 |
| gacgcctgga gcggcctgag gcacgtggtg cagcttcgtg cccaggagga gttcgggcaa | 900 |
| ggcgagtgga gcgagtggag cccggaggcc atgggcacgc cttggacaga atccaggagt | 960 |
| cctccagctc gaggaggtgg aggttctgga ggtggaggtt ctgtcgagcc agtaccccca | 1020 |
| ggagaagatt ccaaagatgt agccgcccca cacagacagc cactcacctc ttcagaacga | 1080 |
| attgacaaac aaattcggta catcctcgac ggcatctcag ccctgagaaa ggagacatgt | 1140 |
| aacaagagta acatgtgtga aagcagcaaa gaggcactgg cagaaaacaa cctgaacctt | 1200 |
| ccaaagatgg ctgaaaaaga tggatgcttc caatctggat tcaatgagga cttgcctg | 1260 |
| gtgaaaatca tcactggtct tttggagttt gaggtatacc tagagtacct ccagaacaga | 1320 |
| tttgagagta gtgaggaaca agccagagct gtgcagatga gtacaaaagt cctgatccag | 1380 |
| ttcctgcaga aaaggcaaa gaatctagat gcaataacca cccctgaccc aaccacaaat | 1440 |
| gccagcctgc tgacgaagct gcaggcacag aaccagtggc tgcaggacat gacaactcat | 1500 |
| ctcattctgc gcagctttaa ggagttcctg cagtccagcc tgagggctct tcggcaaatg | 1560 |